(12) United States Patent
Kumar et al.

(10) Patent No.: US 6,476,220 B2
(45) Date of Patent: Nov. 5, 2002

(54) PROCESS FOR THE PREPARATION OF FURACA

(75) Inventors: Uthira Kumar, Hyderabad (IN); Meenakshisunderam Sivakumaran, Hyderabad (IN); Vijay Kumar Handa, Hyderabad (IN)

(73) Assignee: Aurobindo Pharma Limited, Hyderabad (IN)

( * ) Notice: Subject to any disclaimer, the term of this patent is extended or adjusted under 35 U.S.C. 154(b) by 0 days.

(21) Appl. No.: 09/902,512

(22) Filed: Jul. 9, 2001

(65) Prior Publication Data

US 2002/0065412 A1 May 30, 2002

(30) Foreign Application Priority Data

Nov. 27, 2000 (IN) .................................. 1005MAS/2000

(51) Int. Cl.$^7$ ............................................. C07D 501/36
(52) U.S. Cl. ...................................................... 540/226
(58) Field of Search ......................................... 540/226

(56) References Cited

U.S. PATENT DOCUMENTS 4,463,173 A * 7/1984 Jung ........................... 540/215

\* cited by examiner

*Primary Examiner*—Mark L. Berch
(74) *Attorney, Agent, or Firm*—Jay Akhave

(57) ABSTRACT

A process is disclosed for the preparation of 7-amino-3-(2-furanylcarbonylthiomethyl)-3-cephem-4-carboxylic acid (also known as Furaca). The process comprises of the steps of reacting 7-aminocephalosporanic acid with a mixture of 2-thiofuric acid and Boron Trifluoride in a solvent and precipitating Furaca as a solid.

3 Claims, No Drawings

PROCESS FOR THE PREPARATION OF FURACA

BACKGROUND OF THE INVENTION

The present invention relates to preparation of 7-amino-3-(2-furanylcarbonylthiomethyl)-3-cephem-4-carboxylic acid of the formula

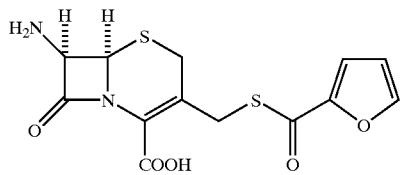

Herein further referred to as Furaca, which is a key intermediate useful in the manufacture of ceftiofur, a cephalosporin antibiotic used for treating bovine respiratory disease.

FIELD OF INVENTION

Process or making ceftiofur intermediate by a novel route in high yield and high purity.

DESCRIPTION OF RELATED ART

U.S. Pat. No. 4,464,367 by Labeeuw teaches a process of preparation of ceftiofur. Ceftiofur was synthesized by condensing activated syn isomer of (2-tritylamino-4-thiazolyl)-2-methoxyimino acetic acid of the formula

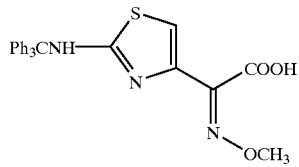

with Furaca in presence of triethylamine to yield tritylceftiofur which on further treatment with aqueous formic acid yielded ceftiofur.

The only known method for the preparation of Furaca is taught by Sacks et al in U.S. Pat. No. 4,937,330. Sacks teaches an aqueous solution of sodium 2-thiofuroate of the formula

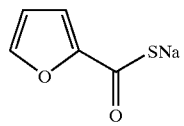

to be reacted with 7-aminocephalosporonic acid at 65° C. at pH of 6.4 +/−0.2 resulting in a slurry which is adjusted to a pH of 5.0, filtered and washed successively with acetone and heptane to obtain a light colored product. The yield of this reaction is not stated.

The Sacks procedure has certain disadvantages, in that it results in impure Furaca in a low yield. Further, the product obtained is colored and contains unreacted 7-aminocephalosporanic acid. This product is not suited or ill-suited for subsequent 7-acylation to produce ceftiofur. The displacement of the acetoxy group of a cephalosporin by a sulfur nucleophile or its salt in an aqueous medium at elevated temperature (65° C.) and near neutral to basic pH is generally destructive to the cephalosporin nucleus and is accompanied by the formation of highly colored impurities. Such a product prepared in this taught manner often requires extensive costly purification.

In addition, the displacement of acetoxy group of a cephalosporanic acid by a sulfur nucleophile in an organic solvent under essentially anhydrous conditions is well documented in literature and in U.S. Pat. No. 4,144,391. Further, it is known from German Offenlegungsschrift 2,804,896 that 7-amino-3-(substituted thiomethyl)-3-cephem-4-carboxylic acids can be prepared by reacting 7-aminocephalosporanic acid with thiol compound in the presence of boron trifluoride. If 2-thiofuroic acid of the formula

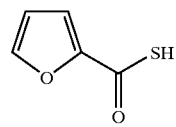

is employed as the thiol compound in the process, with the usual acetonitrile solvent, the reaction is complicated by the formation of desacetyl-7-aminocephalosporanic acid lactone of the formula

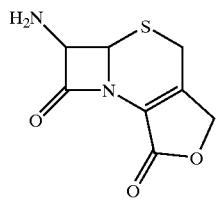

and considerable amount of other unidentified impurities.

Above discussion represents the difficulties with the current art of making Furaca and it is in light of these difficulties that the present invention finds a new route to making Furaca of high purity and high yield.

BRIEF SUMMARY OF THE INVENTION

The present invention provides a novel method of preparation of Furaca of high purity (98–99%) and in good yield (85–88%) by the novel use of boron trifluoride in ethyl acetate. Furaca so obtained can be preferably used for the preparation of antibacterial ceftiofur.

DETAILED DESCRIPTION OF THE INVENTION

Based on our related art disclosure in the background, the present inventors have conducted extensive experimentation with an intention to overcome the difficulties of producing Furaca in high yields and high purity. We have unexpectedly found that such a novel nucleophilic displacement proceeds well in the presence of boron trifluoride in ethyl acetate solvent giving a ceftiofur intermediate of purity of 98–99% with a color rating of 0.04–0.08 (1% solution, 420 nm). The invention further advantageously uses solution of 2-thiofuric acid in ethyl acetate having water to the extent of 4% w/w. Use of a such a solution avoids the isolation of labile 2-thiofuric acid in an anhydrous form reducing the number of process steps increasing safety and cost-effectiveness.

In accordance with the present invention, there is provided a new process for producing Furaca by reacting 7-aminocephalosporanic acid with 2-thiofuroic acid in presence of boron trifluoride. As a rule, boron trifluoride is used in molar excess, 3 to 7 moles of boron trifluoride per mole of 7-aminocephalosporanic acid. The reaction is effected in ethyl acetate in the temperature range of 10° C. to 50° C., preferably between 30° C. to 35° C.

According to the present invention, the boron trifluoride content in ethyl acetate is about 32% w/v. However, varying concentrations can be used depending upon the choice of solvent medium without affecting the final outcome of the process. Typical solvents that can be used are methyl acetate, ethyl acetate, n-butyl acetate and isopropyl acetate. The reaction can be continued until the content of unreacted 7-aminocephalosporanic acid is less than 1% by HPLC analysis. This degree of conversion usually takes about 3 to 5 hours. After the reaction is completed as per HPLC analysis, the reaction mixture is diluted with cold water and subsequently the pH is adjusted with a suitable base such as triethylamine, tributylamine but preferably aqueous ammonia upon which the reaction product precipitates and is obtained in the high purity and yield mentioned before.

The following three examples represent our best mode in our experiments conducted that serves to illustrate our invention without limiting it.

EXAMPLE 1

Step A- Prep of 2-Thiofuroic Acid 35.65 g of sodium sulfide (55%) is dissolved in 545 ml. of water at 25–27° C. The pH of the solution is adjusted to 9.8–10.0 with 85% orthophosphoric acid. 29.1 g of 2-Furoyl chloride is added slowly in 30 mins. while maintaining the pH of solution at 9.0–9.5 with 25% sodium hydroxide solution. The reaction mass is stirred for 1 h at 28–30° C. Thereafter, pH of the reaction mass is lowered to 1.0 with 6N hydrochloric acid. Thiofuroic acid is extracted in 250 ml. of ethyl acetate.

Step B- Prep of Furaca

A solution of 73.3 g of boron trifluoride in 225 ml of ethyl acetate (32% w/v solution) is prepared at 0–5° C. To Thiofuroic acid solution from Step A is added followed by 50 g of 7-aminocephalosporanic acid at 10–15° C. Thereafter the reaction is continued for 3–4 hours at 30–35° C. until the qualitative HPLC analysis shows 7-aminocephalosporanic acid at not more than 1%. The mixture is then cooled to 15° C. and 285 ml of cold water are added followed by freshly prepared solution of 5 g. of sodium metabisulphite in 20 ml water and 0.5 g EDTA disodium in 20 ml water. Immediately the pH of the reaction mass is brought to 2 with 15% aqueous ammonia and then the pH of the reaction mass is slowly adjusted to 5.0 in 30 mins. at 20° C.–25° C. upon which the product precipitates. After stirring for 30 min at 20°–25° C. the product is filtered off under suction and washed with 200 ml ethyl acetate followed by 200 ml of water. The recovered crystals are dissolved in 625 ml of water at pH of 9.0–9.5 by adding 29 ml. of triethylamine slowly in 30 mins at 4° C.–5° C. The aqueous solution is treated with 5 g activated carbon. The carbon is removed and the filtrate is brought to pH of 5.8 very slowly in about 2 hours at 28° C. to 30° C. with addition of 15% aqueous orthophosphoric acid. The product is filtered off and washed with 125 ml water followed by 100 ml acetone and dried under reduced pressure to obtain 53.75 g Furaca (yield of 86%). Purity 99.4%;7-ACA at 0.07% in accordance with HPLC analysis; color at 0.05 (1% solution, 420 nm).

EXAMPLE 2

The procedure of Example 1 has been repeated with 34% w/v solution of boron trifluoride in n-butyl acetate. The Furaca yield was 52.5 g (84%); purity at 99.3% with HPLC; 7-ACA at 0.18% by HPLC.

EXAMPLE 3

The procedure of Example 1 has been repeated using 22% w/v solution of boron trifluoride in isopropyl acetate. The Furaca yield was 53.3 g (85.3%); purity at 99.5% with HPLC; 7-ACA at 0.1% by HPLC.

We claim:

1. A process to prepare a cephalosporin compound of the formula

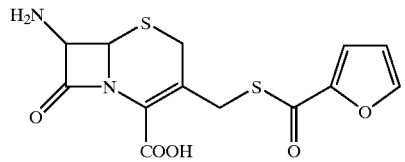

comprising of the steps of:
preparing a catalyst solution of Boron Trifluoride in an organic solvent or in a mixture of organic solvents,
mixing into said catalyst solution of 2-Thiofuric Acid of the formula

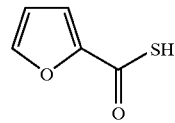

in a solvent to form a reactant mixture,
reacting 7-Aminocephalosporanic acid with the said reactant mixture,
precipitating from the said reaction mixture Furaca as a solid.

2. The process of claim 1 wherein both the said organic solvent and the said mixture of solvents is selected from the group consisting of ethyl acetate, methyl acetate, n-butyl acetate, isopropyl acetate.

3. The process of claim 1 wherein the said reacting step is conducted at a reaction temperature between 10° C. and 50° C.

* * * * *